United States Patent [19]

Clark et al.

[11] Patent Number: 5,679,789
[45] Date of Patent: Oct. 21, 1997

[54] PHARMACEUTICAL COMPOSITIONS COMPRISING POTASSIUM CLAVULANATE AND METHODS OF USING THEM

[75] Inventors: Dennis Edward Clark; Shaukat Hussain Malik; Paul Gerard Butterly, all of Piscataway, N.J.; Clive Elton Badman; Jeffrey David Haseler, both of Worthing, England

[73] Assignee: Beecham Group, p.l.c., Brentford, United Kingdom

[21] Appl. No.: 480,099

[22] Filed: Jun. 7, 1995

Related U.S. Application Data

[60] Division of Ser. No. 151,548, Nov. 12, 1993, abandoned, which is a continuation-in-part of Ser. No. 74,944, Jul. 17, 1987, abandoned, which is a continuation-in-part of Ser. No. 8,781, Jan. 29, 1987, abandoned.

[51] Int. Cl.[6] .............................................. C07D 498/047
[52] U.S. Cl. ...................... 540/349; 540/344; 540/347; 424/114
[58] Field of Search ............................. 540/349, 344, 540/347; 424/114

[56] References Cited

U.S. PATENT DOCUMENTS 4,454,069  6/1984  Cook et al. ........................ 260/245.3

*Primary Examiner*—Samuel A. Acquah
*Assistant Examiner*—Duc Truong
*Attorney, Agent, or Firm*—Janice E. Williams; Edward T. Lentz

[57] ABSTRACT

Potassium clavulanate exists in a novel crystalline habit, namely in the form of rosettes, having improved processing properties. The novel form may, for example, be obtained by crystallization or recrystallization using inverse precipitation, preferably at 8°–15° C.

8 Claims, 4 Drawing Sheets

PHARMACEUTICAL COMPOSITIONS COMPRISING POTASSIUM CLAVULANATE AND METHODS OF USING THEM

CROSS-REFERENCE

This is a division of Ser. No. 151,548 filed Nov. 12, 1993 now abandoned which is a continuation-in-part of application Ser. No. 07/074,944 filed Jul. 17, 1987 (D. E. Clark, S. H. Malik, P. G. Butterly) now abandoned which is a continuation-in-part of application Ser. No. 07/008,781 filed Jan. 29, 1987 (D. E. Clark, S. H. Malik, P. G. Butterly), now abandoned, both of which applications are incorporated herein by reference thereto.

The present invention relates to a novel crystalline form of potassium clavulanate having improved properties.

Clavulanic acid and its salts are described in British Patent Specification No. 1 508 977 (the contents of which is incorporated herein by reference thereto) as β-lactamase inhibitors capable of enhancing the antibacterial effects of β-lactam antibiotics, such as penicillins and cephalosporins. Antibacterial compositions comprising potassium clavulanate and amoxycillin are commercially available under the trade name 'Augmentin' (registered Trade Mark of Beecham Group p.l.c.), and certain oral dry unit-dose antibacterial compositions of potassium clavulanate and amoxycillin are described in British Patent Specification No. 2 005 538. Antibacterial compositions comprising potassium clavulanate and ticarcillin are commercially available under the trade name 'Timentin' (registered Trade Mark of Beecham Group p.l.c). Potassium clavulanate may also be formulated with other penicillins and cephalosporins to enhance their antibacterial efficacy, and may be formulated alone for separate co-administration with penicillins and cephalosporins.

Crystalline potassium clavulanate generally exists in the form of rod-like or needle-like crystals, which are generally relatively large, long crystals, sometimes agglomerated into plate-like crystals, and sometimes randomly aggregated into loosely formed bundles. This form of potassium clavulanate can give rise to processing difficulties in that the material does not always flow readily, is of low bulk density, and can be difficult to sieve. We have now found that potassium clavulanate can exist in another crystalline habit having improved processing characteristics.

Accordingly, the present invention now provides crystalline potassium clavulanate being in the form of crystalline rosettes each comprising a plurality of needle crystals radiating out from a common nucleation point.

The rosette-form of crystalline potassium clavulanate, as defined above, has improved flow characteristics as compared with the standard needle-form potassium clavulanate. It also has improved sieving characteristics in that over 90% by weight of the material, generally over 95% by weight of the material, can readily be passed through an 850 µm (number 20) mesh screen, whereas with the conventional needle form of the material generally about 30% by weight fails to pass through an 850 µm mesh screen. Consequently, the rosette form of the material has considerable advantages for pharmaceutical processing and formulation.

Accordingly to one aspect of the present invention, the rosette-form of crystalline potassium clavulanate is provided in substantially pure form, that is to say that the said rosette material contains not more than 50% by weight, advantageously not more than 25% by weight, preferably not more than 20% by weight, more preferably not more than 15% by weight, especially not more than 10% by weight, more especially not more than 5% by weight, yet more especially not more than 2% by weight, and very especially not more than 1% by weight of other crystalline forms or habits of potassium clavulanate, especially the conventional needle form (all percentages being based on the total weight of the material).

According to another aspect of the present invention, the rosette-form of crystalline potassium clavulanate is provided substantially free of admixture with other material, especially of other pharmaceutically active material, including in particular antibacterially active materials, especially penicillins, for example ticarcillin. In this context, the expression 'substantially free of' means admixed with not more than 100% by weight, advantageously not more than 75% by weight, preferably not more than 50% by weight, especially not more than 25% by weight, of said other materials, all percentages being based on the weight of the potassium clavulanate.

The rosette form of potassium clavulanate according to the present invention may have a bulk density within the range of from 0.2 to 0.8 g/cm$^3$, advantageously from 0.2 to 0.6 g/cm$^3$, such as from 0.2 to 0.5 g/cm$^3$, for example from 0.3 to 0.5 g/cm$^3$.

In the rosette-form material according to the present invention, generally at least 80%, advantageously at least 90%, preferably at least 95%, and more preferably at least 99%, by volume of the material has a particle size exceeding 1280 µm$^2$, with generally at least 65%, advantageously at least 75%, preferably at least 80%, and more preferably at least 90%, by volume of the material having a particle size exceeding 5120 µm$^2$. In contrast thereto, with needle-form material, generally at least 50%, and normally at least 60%, by volume of the material has a particle size below 1280 µm$^2$, with generally at least 75%, and normally at least 85%, by volume of the material having a particle size below 5120 µm$^2$. The particle size of the material may conveniently be determined by image analysis.

In the rosette-form material according to the invention the individual rosettes are thought to consist of a plurality of small needle crystals radiating out from a common nucleation point: radiating clusters of crystals. This appears to be borne out by the fact that X-ray diffractograms show no significant difference in crystal structure between the rosette material and the standard needle-form material.

The individual needles in the rosettes may be extremely small and fine and may not be microscopically distinguishable under even 100-fold magnification: the rosettes may appear simply as small 'roses' or spheres with little or no visible surface crystal growth. In other cases a small amount of needle-like crystal growth will be microscopically visible at the circumference of the rosettes, and in some cases the rosette will appear as a hard core with a large number of visible small radiating needles. In all cases, however, the rosette form of the material is clearly discernible microscopically and is clearly distinguishable from the standard needle-form material, which, under 100-fold magnification, clearly appears as such, for example as randomly arranged long thin needles.

Thus the particular crystalline habit of any given sample of potassium clavulanate can readily be ascertained simply by microscopic examination under, say, 100-fold magnification.

In the rosettes, the individual needle crystals may radiate out from the common nucleation point in a single plane or in a plurality of planes. Also, they may radiate out in certain directions only or in all directions. Thus, the individual needles may radiate out from the central nucleation point to form, for example, a full or part circle or a full or part sphere. Two or more individual rosettes may, of course, agglomerate together.

In many cases, particularly when the rosette surface has microscopically visible surface growth, the rosettes can be broken down (for example by trituration with liquid paraffin in an agate pestle and mortar) at least partially into the constituent individual fine needle crystals. In such cases, it is apparent both microscopically and by particle size determination that the constituent needles are much smaller and more fine that the needles of standard needle-form material. For example, in cases where it is possible to break the rosettes down substantially, generally at least 75% by volume of the broken-down material will have a particle size below 1280 μm², with generally at least 95% of the material having a particle size below 5120 μm².

In some cases, particularly when the rosettes appear microscopically simply as small 'roses' or spheres with no visible surface growth, the rosettes may be too hard and compact to be broken down in the manner described above. Nevertheless, X-ray diffractograms still show the basic crystal form to be essentially needle-like and it is still apparent from microscopic inspection that the crystal habit is fundamentally different from that of standard needle-form material.

It has been found that the precise form of the rosettes— that is to say, for example, whether or not there is visible surface crystal growth, whether the rosettes are hard or soft, whether they are compact or more open, whether they are largely full or partial rosettes, and whether they are agglomerated—depends, inter alia, on the precise method used for their preparation. In all cases, however, it is clearly apparent from microscopic inspection, and also from particle size determination, that the material is in rosette form.

The present invention also provides a process for the preparation of rosette-form crystalline potassium clavulanate, which comprises causing potassium clavulanate to crystallise from solution under such conditions that the rosette-form is precipitated.

In particular, rosette-form crystalline potassium clavulanate may be prepared by adding a solution of clavulanate ions to a non-solvent for potassium clavulanate, in the presence of potassium ions, advantageously at a temperature not exceeding 15° C.

The clavulanate ions may suitably be provided in the form of potassium clavulanate, in which case that will also be the source of the potassium ions. In this case, the process will be a crystallisation or recrystallisation process.

The form of the potassium clavulanate used as starting material for the crystallisation or recrystallisation is not critical and it may for example be needle-form crystalline material, rosette-form crystalline material, or amorphous material. It should advantageously be of high purity.

The clavulanate ions may alternatively be provided in the form of another clavulanate salt, for example tert-butylamine clavulanate. In this case, the potassium ions will be provided from another source and may be provided in the clavulanate solution or, advantageously, in the precipitating diluent (that is to say, the non-solvent for potassium clavulanate). The potassium ions may, for example, conveniently be provided in the form of potassium ethyl hexanoate.

The potassium ions should, of course, be present in an at least equivalent amount with respect to the clavulanate ions. This criteria will, of course, be satisfied when the potassium ions are provided by potassium clavulanate. When using another clavulanate salt with a separate source of potassium ions, the potassium ions are preferably present in excess, for example up to 1.5 equivalents, with respect to the clavulanate ions.

It has been found that for reliable obtension of the rosette form the precipitation should be effected by so-called 'inverse' or 'reverse' precipitation, that is to say the clavulanate solution is added to the precipitating diluent, in contrast to the 'normal' precipitation procedure in which the precipitating diluent is added to the solution of the material to be crystallised.

The solvent used for dissolution of the clavulanate ions may be any convenient solvent in which the particular clavulanate salt is soluble and which is compatible with the chosen precipitating diluent. Suitable solvents are especially aqueous alcohols, preferably an aqueous alkanol, more preferably an aqueous $(C_{1-6})$alkanol, for example aqueous methanol, aqueous ethanol, or aqueous isopropanol, as well as mixtures of two or more thereof, for example aqueous methanol/isopropanol. The aqueous content of the aqueous alcohol is suitably from 5 to 25% by volume.

The diluent used for precipitation of the potassium clavulanate may be any convenient non-solvent for potassium clavulanate which is compatible with the chosen dissolution solvent. Advantageously, the precipitating diluent is isopropanol or a mixture of isopropanol and acetone (up to 10:90 by volume).

Suitable combinations of solvent and precipitating diluent may readily be ascertained by simple trial experiments if necessary.

One method that has been found particularly suitable is to dissolve potassium clavulanate in aqueous methanol (suitably 75% to 95% methanol, preferably about 80% methanol) and then to initiate precipitation by addition of the resulting solution to a mixture of isopropanol and acetone (suitably about 3 volumes of isopropanol to 1 volume of acetone), according to the reverse precipitation procedure. According to one embodiment of this method, the precipitation may be carried out at a temperature within the range of from 0° to 10° C., and according to another embodiment of this method the precipitation may be carried out at a temperature within the range of from 10° to 15° C.

An alternative method involves recrystallisation of potassium clavulanate by dissolution in aqueous ethanol, followed by reverse precipitation in isopropanol/acetone (preferably about 3:1).

It is also possible to obtain the rosette-form material by dissolution of potassium clavulanate in aqueous isopropanol (preferably about 80-85% isopropanol) followed by reverse precipitation in isopropanol or with isopropanol/acetone (preferably about 3:1).

Another particularly suitable method for obtaining the desired rosette-form material is to dissolve tert-butylamine clavulanate in an aqueous solvent selected from isopropanol, methanol and mixtures thereof (suitably up to 25% by volume of water in each case), followed by addition of the resulting solution to a solution of potassium ions (suitably as potassium ethyl hexanoate) in a solvent selected from isopropanol and isopropanol/acetone (up to 90% by volume of acetone) so as to cause precipitation of potassium clavulanate in the form of crystalline rosettes.

In one embodiment of this method, tert-butylamine clavulanate is dissolved in aqueous methanol or in aqueous methanol/isopropanol (from 5 to 25% by volume of water in each case), followed by addition of the resulting clavulanate solution to a solution of potassium ethyl hexanoate in isopropanol or in isopropanol/acetone (up to 90% by volume of acetone).

In a second embodiment of this method, a solution of tert-butylamine clavulanate in aqueous isopropanol (from 2 to 10%, preferably about 5%, by volume of water) is prepared, and the resulting clavulanate solution is added to a solution of potassium ethyl hexanoate in isopropanol.

In all cases the pH of the clavulanate solution is advantageously about 6.5 to 7.0 preferably slightly below 7.0, suitably from 6.5 to 6.9. Where necessary, the pH may suitably be adjusted by the addition of, for example, acetic acid.

It can also be advantageous to treat the clavulanate solution with decolourising charcoal, with subsequent filtration, prior to precipitation.

Precipitation is advantageously effected at a temperature not exceeding 15° C., advantageously from 0° C. to 15° C., more advantageously from 5° C. to 15° C., preferably from 8° C. to 15° C., and especially from 10° C. to 15° C. It has been found that the use of such a temperature is advantageous in consistently giving the desired rosette-form of the product.

The rosette-form material according to the present invention may be dried, processed and formulated in a manner conventional for potassium clavulanate, but with the particular advantages discussed above.

Thus, the present invention also provides a pharmaceutical composition comprising rosette-form potassium clavulanate as herein defined in admixture or conjunction with a pharmaceutically acceptable carrier or excipient.

The present invention also provides a pharmaceutical composition comprising rosette-form potassium clavulanate as herein defined in admixture or conjunction with an antibacterially active β-lactam compound, especially a penicillin or cephalosporin.

A pharmaceutical composition according to the present invention may be adapted for oral or parenteral use, and may be used for the treatment of bacterial infections in mammals, including humans.

A composition according to the invention may, for example, be in the form of tablets, capsules, granules, suppositories, suspensions, or reconstitutable powders (for subsequent dissolution to form solutions for injection or infusion).

Injectable or infusable compositions, for example reconstitutable powders, of clavulanic acid and its salts are particularly important as they can give high tissue levels of the compound after administration by injection or infusion. Thus, one preferred composition aspect of the present invention comprises rosette-form potassium clavulanate in sterile form, optionally in admixture or conjunction with an antibacterially active β-lactam compound in sterile form. Such compositions may, for example, be stored in sterile vials until use. In accordance with conventional practice, such reconstitutable powders may be dissolved in a sterile pyrogen-free liquid such as water for injection B.P..

The compositions according to the invention—whether for oral or parenteral use—may be in unit dosage form. For example, a unit dose of a reconstitutable powder may be contained within a sterile vial for subsequent dissolution to give a single injectable dose.

Preferred penicillins for use in admixture or conjunction with rosette-form potassium clavulanate according to the present invention include ticarcillin and amoxycillin and pharmaceutically acceptable salts and in-vivo hydrolysable esters thereof.

Further details of formulating potassium clavulanate into pharmaceutical compositions, as well as details of dosages, and details of other antibacterially active β-lactam compounds for co-use with potassium clavulanate are given in British Patent Specification No. 1 508 977 and such details are also applicable to the rosette-form of the material according to the present invention.

According to further aspects, the present invention provides:

the use of rosette-form potassium clavulanate for the treatment of bacterial infections;

the use of rosette-form potassium clavulanate in admixture or conjunction with an antibacterially active β-lactam compound for the treatment of bacterial infections;

the use of rosette-form potassium clavulanate in the preparation of a medicament for the treatment of bacterial infections, the medicament preferably being suitable for administration by injection or infusion;

a method for the treatment of a bacterial infection in a human or animal patient, which comprises co-administering thereto an antibacterially effective amount of rosette-form potassium clavulanate and an antibacterially active β-lactam compound;

a method for the treatment of a bacterial infection in a human or animal patient, which comprises administering thereto an antibacterially effective amount of an antibacterially active β-lactam compound and a β-lactamase inhibitory amount of rosette-form potassium clavulanate; and rosette-form potassium clavulanate with the proviso that it is not admixed solely with sodium ticarcillin in a ratio of 1:30 by weight, calculated as free acid clavulanic acid:ticarcillin free acid, in the form of a sterile reconstitutable powder, in a vial.

The following examples and the accompanying figures illustrate the present invention.

BRIEF DESCRIPTION OF THE DRAWINGS

In FIGS. 1 to 4, the magnification of the microphotographs is approximately 100-fold.

In FIGS. 5 to 11, 1 scale division denotes 15 μm.

Figure 1:
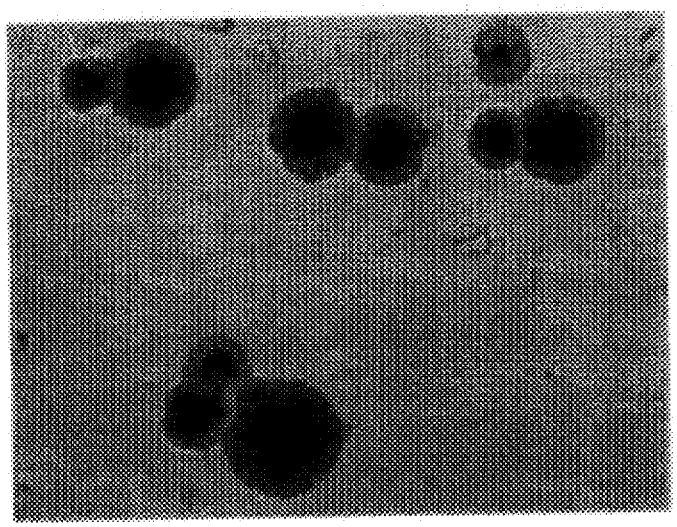
FIGS. 1–5, 8 and 10 show microphotographs of various samples rosette-form potassium clavulanate, as further explained in the examples.
Figure 2:
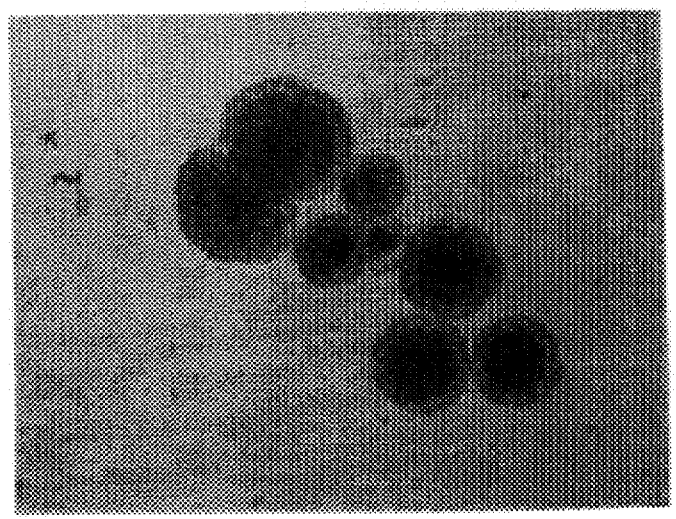
Figure 3:
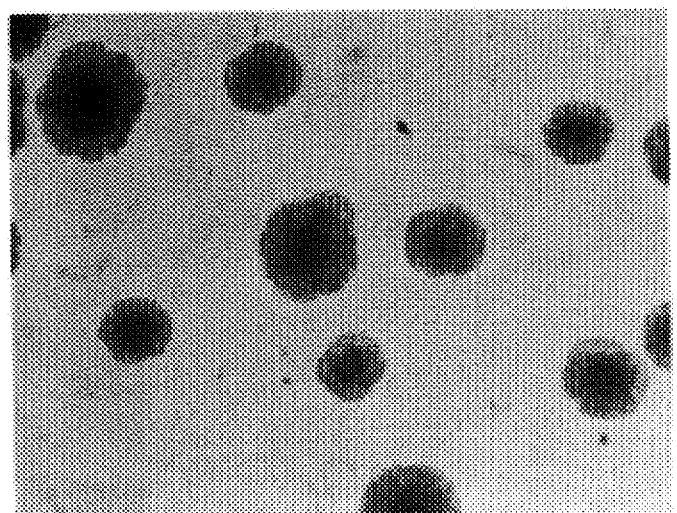
Figure 4:
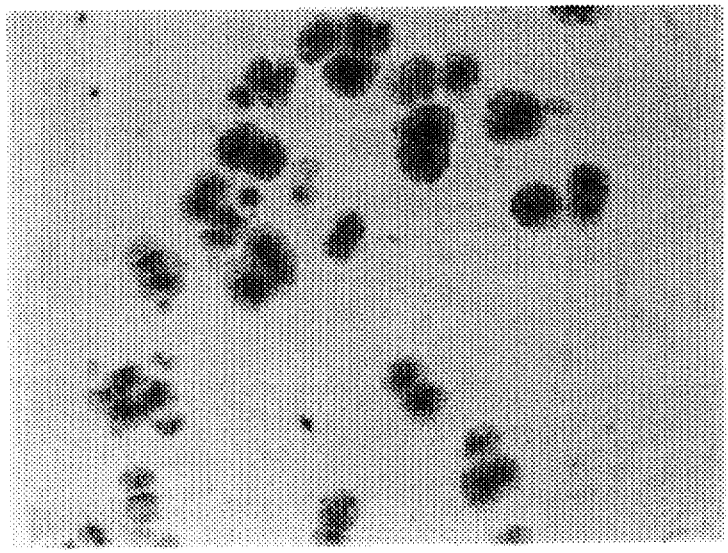

In the examples and comparison examples, the particle sizes of the products were determined using an AMS (Analytical Measuring Systems) System III Image Analyser, using a Zeiss Lens with Plan 6.3.

EXAMPLE 1

24 g of potassium clavulanate is added to a mixture of methanol (50 ml), glacial acetic acid (0.37 ml) and water (11 ml) at 18°–20C. and stirred for 10 minutes at 18°–20° C. The pH of the solution is checked to confirm it as 6.5–6.9. 2.4 g of charcoal (Norit) is added to the solution. The solution is stirred for 20 minutes, and then filtered over filter-aid into a 125 ml dropping funnel. The filtrate is added to 600 ml isopropanol/acetone (3:1) at 10°–15C. over 20 minutes. The filter funnel and dropping funnel are washed with 10% H₂O/MeOH (25 ml) and the wash added to the suspension. The suspension is stirred for 1 hour at 10°–15° C. and then for 1 hour at 0°–5C. The product is filtered, washed with two portions of acetone (50 ml each), and dried in a vacuum oven (27–28 inches Hg) with a dry air bleed at 25° C. overnight.

The following data summarises results obtained by carrying out the above recrystallisation procedure on a number of samples of potassium clavulanate:

Weight: 21.6 g (average)
Assay: 82–84% (from input assay of 80–84%; theoretical assay 83.9%)
Yield: 89–92%
Moisture Content: 0.5%
Crystal form: Rosettes
Bulk density: 0.29–0.46 g/cm$^3$ The accompanying FIGS. 1 to 4 show microphotographs (100-fold magnification) of four samples of potassium clavulanate recrystallised by the above procedure.

EXAMPLE 2

Figure 5:
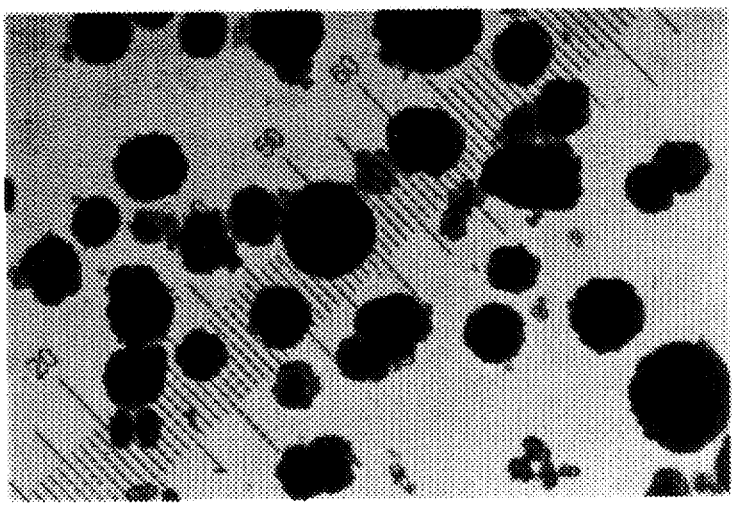

A further sample of potassium clavulanate was recrystallised using the procedure of Example 1. The product was of rosette crystal form and had a bulk density of 0.53 g/cm$^3$. FIG. 5 shows a microphotograph of the product.

The particle size of two samples of the resulting rosette material was determined by image analysis. The results are given in Table 1.

Figure 6:
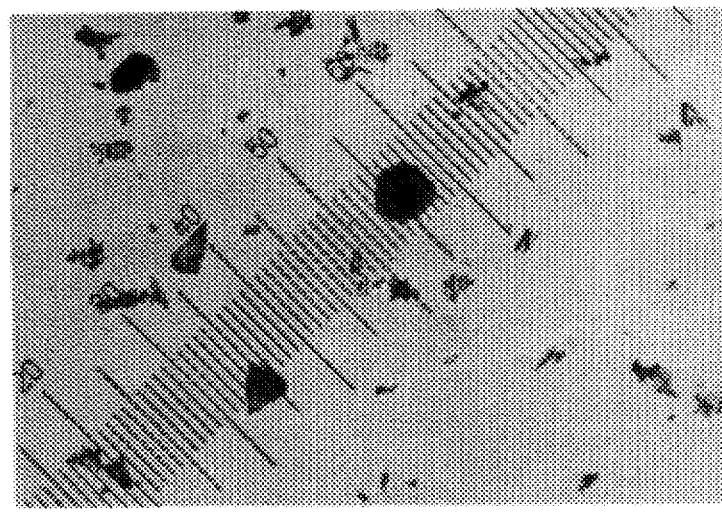
FIGS. 6, 9 and 11 show microphotographs of the samples of FIGS. 5, 8 and 10 subsequent to the rosettes being broken down, as further explained in Examples 2, 7 and 8.

A portion of the rosette material was triturated with liquid paraffin in an agate pestle and mortar in order to break down the rosette crystal structure. FIG. 6 shows a microphotograph of the broken-down material, from which it can clearly be seen that the rosettes comprise clusters of radiating fine needles.

The particle size of the broken-down material was determined and the results are given in Table 2.

TABLE 1

Particle size of rosette material (Example 2)

| Particle size range | Volume % within range | | Volume % within range and above | |
|---|---|---|---|---|
| (μm$^2$) | Sample 1 | Sample 2 | Sample 1 | Sample 2 |
| 160–320 | 0.44 | 0.48 | 99.95 | 99.96 |
| 320–640 | 0.85 | 0.75 | 99.51 | 99.48 |
| 640–1280 | 1.06 | 1.07 | 98.66 | 98.73 |
| 1280–2560 | 1.37 | 2.64 | 97.60 | 97.66 |
| 2560–5120 | 8.38 | 12.00 | 96.23 | 95.02 |
| 5120–10240 | 36.45 | 36.01 | 87.85 | 83.02 |
| 10240–20480 | 45.23 | 41.13 | 51.40 | 47.01 |
| 20480–40960 | 6.17 | 5.88 | 6.17 | 5.88 |
| >40960 | 0.00 | 0.00 | 0.00 | 0.00 |

TABLE 2

Particle size of broken rosette material (Example 2)

| Partical size range (μm$^2$) | Volume % within range | Volume % within range and above |
|---|---|---|
| 10–20 | 5.25 | 99.96 |
| 20–40 | 10.73 | 94.71 |
| 40–80 | 17.21 | 83.98 |
| 80–160 | 19.62 | 66.77 |
| 160–320 | 19.08 | 47.15 |
| 320–640 | 9.44 | 28.07 |
| 640–1280 | 11.44 | 18.63 |
| 1280–2560 | 7.19 | 7.19 |
| >2560 | 0.00 | 0.00 |

EXAMPLE 3

A further sample of potassium clavulanate was recrystallised using the procedure of Example 1. The product was of rosette crystal form and had a bulk density of 0.25 g/cm$^3$.

The particle size of two samples of the resulting rosette material was determined by image analysis. The results are given in Table 3.

A portion of the rosette material was triturated with liquid paraffin in an agate pestle and mortar in order to break down the rosette crystal structure. The particle size of the broken-down material was determined and the results are given in Table 4.

TABLE 3

Particle size of rosette material (Example 3)

| Particle size range | Volume % within range | | Volume % within range and above | |
|---|---|---|---|---|
| (μm$^2$) | Sample 1 | Sample 2 | Sample 1 | Sample 2 |
| 160–320 | 0.66 | 0.74 | 99.96 | 99.99 |
| 320–640 | 1.54 | 1.70 | 99.30 | 99.25 |
| 640–1280 | 2.88 | 3.50 | 97.76 | 97.55 |
| 1280–2560 | 5.63 | 6.25 | 94.88 | 94.02 |
| 2560–5120 | 9.18 | 9.63 | 89.25 | 87.77 |
| 5120–10240 | 19.54 | 18.09 | 80.07 | 78.14 |
| 10240–20480 | 27.07 | 25.40 | 60.53 | 60.05 |
| 20480–40960 | 29.87 | 28.74 | 33.46 | 34.65 |
| 40960–81920 | 3.59 | 5.91 | 3.59 | 5.91 |
| >81920 | 0.00 | 0.00 | 0.00 | 0.00 |

TABLE 4

Particle size of broken rosette material (Example 2)

| Partical size range (μm$^2$) | Volume % within range | Volume % within range and above |
|---|---|---|
| 10–20 | 0.80 | 99.96 |
| 20–40 | 1.64 | 99.16 |
| 40–80 | 4.12 | 97.52 |
| 80–160 | 8.10 | 93.40 |
| 160–320 | 16.00 | 85.30 |
| 320–640 | 23.00 | 69.30 |
| 640–1280 | 26.02 | 46.30 |
| 1280–2560 | 16.28 | 20.28 |
| 2560–5120 | 4.00 | 4.00 |
| >5120 | 0.00 | 0.00 |

EXAMPLE 4

20 g of t-butylamine clavulanate is added to a mixture of isopropanol (50 ml), water (6 ml), methanol (12 ml), and acetic acid (0.1 ml), at about 20° C. and stirred. The pH of the solution is adjusted to just below 7, with additional acetic acid as necessary. 1 g of charcoal is added to the solution, which is then stirred for 30 minutes, and then filtered over filter-aid, followed by washing with isopropanol (50 ml). The filtrate is added to a filtered mixture of 2N potassium ethyl hexanoate in isopropanol (47 ml), isopropanol (200 ml), and acetone (100 ml) maintained at 8°–10° C. over 15–20 minutes. The filter funnel is washed with isopropanol (30 ml) and the wash added to the suspension. The suspension is cooled to 0°–5° C. and stirred for 1 hour. The product is filtered, washed with two portions of acetone (50 ml each), sucked dry through a rubber sheet, and dried in a vacuum oven (27–28 inches Hg) with a dry air bleed at 20° C. for 18 hours.

The following data summarises results obtained by carrying out the above crystallisation procedure from a number of samples of t-butylamine clavulanate:

Weight: 14.7–15.0 g
Assay: 82% (average; theoretical assay 83.9%)
Yield: 90–94%
Crystal form: Rosettes

EXAMPLES 5–7

Three further samples of t-butylamine clavulanate were treated according to the procedure of Example 4 to give rosette-form potassium clavulanate.

Analysis results on the products are summarised in Table 5. The particle size: of the products was determined by image analysis and the results are given in Table 6.

Figure 8:
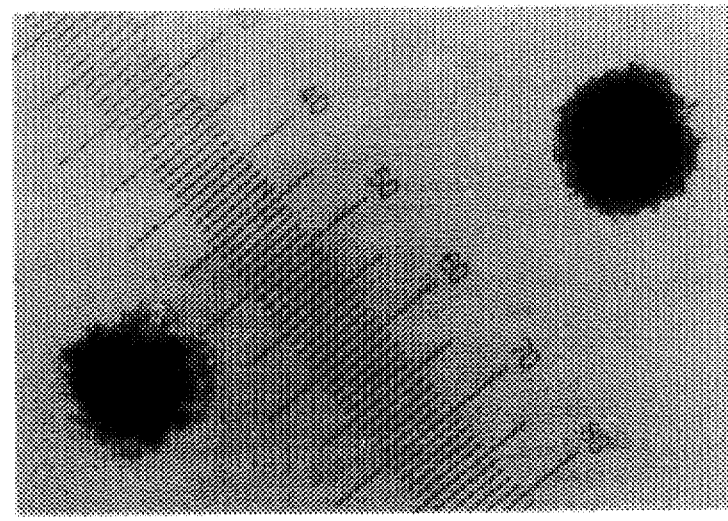
Figure 9:
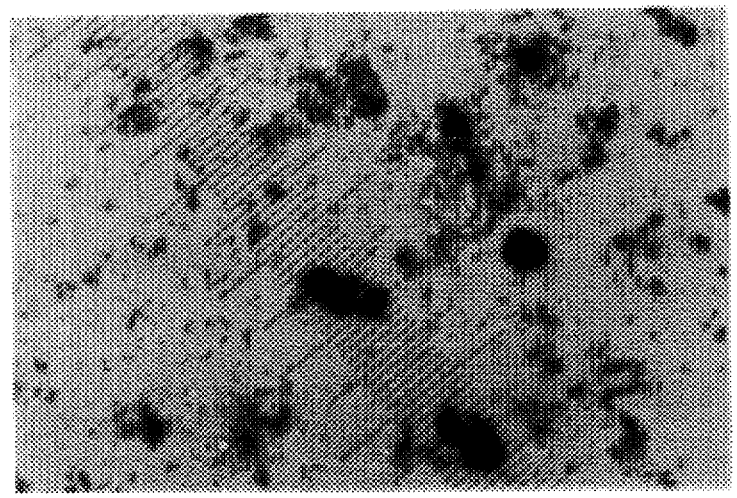

FIG. 8 shows a microphotograph of the product of Example 7 and FIG. 9 shows a microphotograph of a portion of the material of Example 7 which has been broken down by trituration with liquid paraffin in an agate pestle and mortar.

TABLE 5

| Analysis of rosette material (Examples 5–7) | | | |
|---|---|---|---|
| | Example 5 | Example 6 | Example 7 |
| Assay % | 81.84 | 81.61 | 81.75 |
| pH | 7.4 | 7.2 | 7.4 |
| Bulk density g/cm$^3$ | 0.75 | 0.77 | 0.53 |
| Acetone % | 0.24 | 0.32 | 0.24 |
| Methanol % | 0.11 | 0.12 | 0.10 |
| Isopropanol % | 0.25 | 0.32 | 0.25 |
| Water % | 0.30 | 0.28 | 0.25 |
| 2-ethyl hexanoic acid % | 0.58 | 0.59 | 0.43 |
| Clavam 2-carboxylate % | <0.01 | <0.01 | <0.01 |
| t-butyluamine % | <0.05 | <0.05 | <0.05 |
| Physical form | Hard compact rosettes with slight surface crystal growth. Difficult to fracture. Flowed freely. | Very hard compact rosettes with no visible surface crystal growth. Very difficult to fracture. Flowed freely. | Soft rosettes with visible surface crystal growth. Easily fractured. Flowed freely |

TABLE 6

| Particle size range (μm$^2$) | Volume % within range | | | Volume % within range and above | | |
|---|---|---|---|---|---|---|
| | Example 5 | Example 6 | Example 7 | Example 5 | Example 6 | Example 7 |
| 160–320 | 0.01 | 0.00 | 0.00 | 99.96 | 99.95 | 99.95 |
| 320–640 | 0.01 | 0.01 | 0.01 | 99.95 | 99.95 | 99.95 |
| 640–1280 | 0.03 | 0.04 | 0.01 | 99.94 | 99.94 | 99.94 |
| 1280–2560 | 0.11 | 0.13 | 0.01 | 99.91 | 99.90 | 99.93 |
| 2560–5120 | 1.35 | 0.84 | 0.01 | 99.80 | 99.77 | 99.92 |
| 5120–10240 | 6.56 | 5.51 | 0.09 | 98.45 | 98.93 | 99.91 |
| 10240–20480 | 25.27 | 22.41 | 1.69 | 91.89 | 93.42 | 99.82 |
| 20480–40960 | 37.98 | 43.91 | 17.40 | 66.62 | 71.01 | 98.13 |
| 40960–81920 | 28.64 | 24.53 | 54.54 | 28.64 | 27.10 | 80.73 |
| 81920–163840 | 0.00 | 2.57 | 26.19 | 0.00 | 2.57 | 26.19 |
| >163840 | 0.00 | 0.00 | 0.00 | 0.00 | 0.00 | 0.00 |

EXAMPLE 8

1.54 kg of t-butylamine clavulanate (equivalent to 1.00 kg of free acid at 65% purity) is dissolved in a mixture of 5 liters of isopropanol and 0.7 liter of water. After complete dissolution, the solution is filtered and then cooled to 8°–10° C. 7.8 liters of isopropanol is added to 3.52 liters of 2N potassium ethyl hexanoate in isopropanol (about 1.4 mole equivalents), all of which is cooled to 8°–10° C. The cooled tert-butylamine clavulanate solution is then added to the cooled potassium ethyl hexanoate solution, and the resulting slurry is stirred for 2 hours while being cooled to 0°–5° C., and then filtered. The filtrate is washed with isopropanol and then with acetone, after which it is dried.

Figure 10:
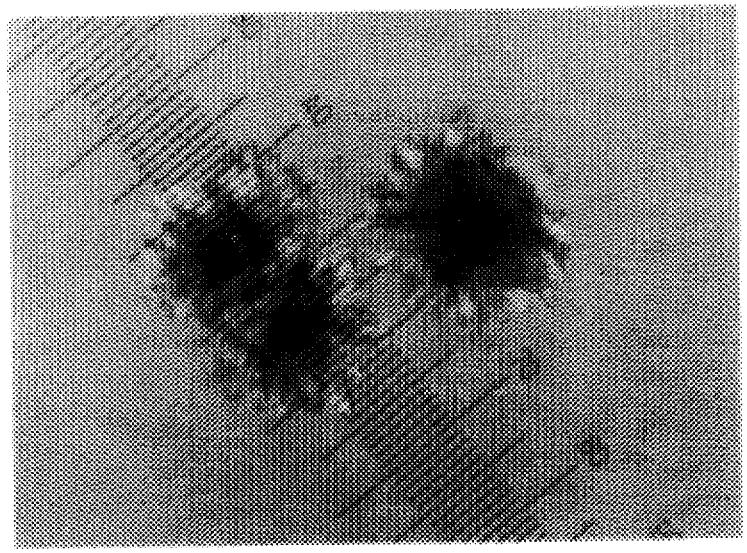

The product was in the form of soft rosettes, showing crystal growth radiating from a relatively hard core. FIG. 10 shows a microphotograph of the product.

Figure 11:
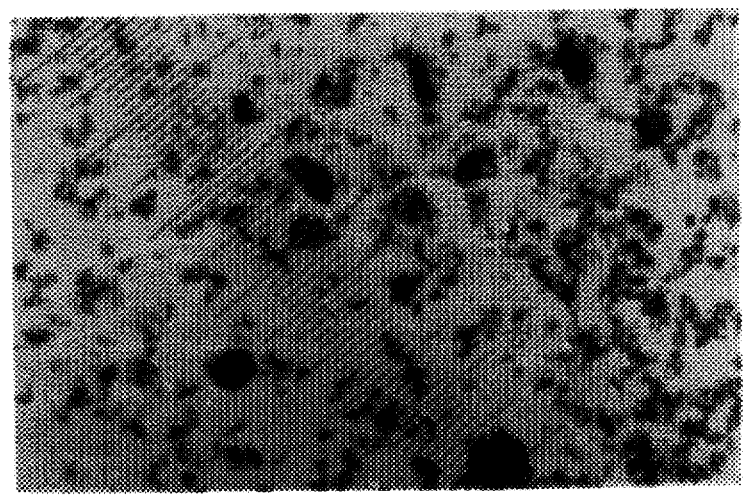

The rosettes were easily fractured, by trituration with liquid paraffin in an agate pestle and mortar, to give a mass of small crystals, as shown in FIG. 11.

The product was free flowing, and had a bulk density of 0.35 g/cm$^3$.

The particle size of the product was determined by image analysis and the results are given in Table 7.

TABLE 7

| Particle size of rosette material (Example 8) | | |
|---|---|---|
| Partical size range (μm$^2$) | Volume % within range | Volume % within range and above |
| 160–320 | 0.00 | 99.95 |
| 320–640 | 0.00 | 99.95 |
| 640–1280 | 0.01 | 99.95 |
| 1280–2560 | 0.04 | 99.94 |
| 2560–5120 | 1.90 | 99.90 |
| 5120–10240 | 24.88 | 98.00 |
| 10240–20480 | 58.84 | 73.12 |
| 20480–40960 | 13.69 | 14.28 |
| 40960–81920 | 0.59 | 0.59 |
| >81920 | 0.00 | 0.00 |

COMPARISON EXAMPLES A AND B

Two samples of the conventional crystalline form of potassium clavulanate in large individual needles (which may, in some cases, be randomly formed into loosely bound aggregates) were subjected to particle size determination by image analysis. The results are given in Table 8.

Figure 7:
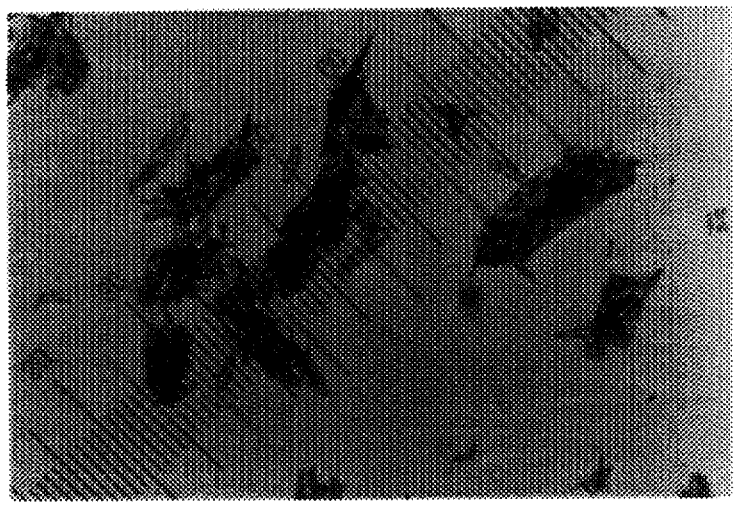
FIG. 7 shows, for comparison purposes, a microphotograph of a sample of the conventional crystalline form of potassium clavulanate in large individual needles, which are in some cases randomly formed into loosely bound aggregates, as further explained in the Comparison Example.

FIG. 7 shows a microphotograph of the sample of comparison Example A.

TABLE 8

Particle size of needle-form material (Comparison)

| Particle size range ($\mu m^2$) | Volume % within range | | Volume % within range and above | |
|---|---|---|---|---|
| | Example A | Example B | Example A | Example B |
| 10–20 | 0.83 | 1.94 | 99.97 | 99.93 |
| 20–40 | 2.64 | 3.41 | 99.14 | 97.99 |
| 40–80 | 5.73 | 4.91 | 96.50 | 94.58 |
| 80–160 | 9.65 | 8.02 | 90.77 | 89.67 |
| 160–320 | 14.51 | 13.40 | 81.12 | 81.65 |
| 320–640 | 15.98 | 16.01 | 66.61 | 68.25 |
| 640–1280 | 18.08 | 18.90 | 50.63 | 52.24 |
| 1280–2560 | 21.48 | 19.89 | 32.55 | 33.34 |
| 2560–5120 | 2.89 | 3.51 | 11.07 | 13.45 |
| 5120–10240 | 8.18 | 9.94 | 8.18 | 9.94 |
| >10240 | 0.00 | 0.00 | 0.00 | 0.00 |

We claim:

1. A pharmaceutical composition comprising crystalline potassium clavulanate in admixture with an antibacterially active β-lactam compound, wherein the potassium clavulanate is in the form of crystalline rosettes, each rosette comprising a plurality of needle crystals radiating out from a common nucleation point and characterized by their microscopic appearance under 100-fold magnification as having a clearly discernable rosette-form.

2. A method for the treatment of a bacterial infection in a human or animal patient, which comprises co-administering thereto an antibacterially effective amount of crystalline potassium clavulanate and an antibacterially active β-lactam compound in admixture, wherein the potassium clavulanate is in the form of crystalline rosettes, each rosette comprising a plurality of needle crystals radiating out from a common nucleation point and characterized by their microscopic appearance under 100-fold magnification as having a clearly discernable rosette-form.

3. A method for the treatment of a bacterial infection in a human or animal patient, which comprises administering thereto an antibacterially effective amount of an antibacterially active β-lactam compound and a β-lactamase inhibitory amount of crystalline potassium clavulanate in admixture, wherein the potassium clavulanate is in the form of crystalline rosettes, each rosette comprising a plurality of needle crystals radiating out from a common nucleation point and characterized by their microscopic appearance under 100-fold magnification as having a clearly discernable rosette-form.

4. A pharmaceutical composition according to claim 1 wherein the antibacterially active beta-lactam compound is amoxycillin or a pharmaceutically acceptable salt thereof.

5. A pharmaceutical composition according to claim 1 in the form of a tablet adapted for oral use.

6. A pharmaceutical composition according to claim 1 in the form of a tablet capsule, granule, suppository, suspension or reconstitutable powder.

7. A pharmaceutical composition according to claim 1 being a formulation for reconstitution into an injectable or infusable composition.

8. A pharmaceutical composition according to claim 1 being an oral dry unit-dose antibacterial formulation in which the antibacterial active beta-lactam compound is amoxycillin.

* * * * *